(12) United States Patent
Imai et al.

(10) Patent No.: US 12,055,243 B2
(45) Date of Patent: Aug. 6, 2024

(54) JOINT UNIT AND METHOD FOR ASSEMBLING JOINT UNIT

(71) Applicant: Surpass Industry Co., Ltd., Gyoda (JP)

(72) Inventors: Hiroshi Imai, Gyoda (JP); Masahiro Hasunuma, Gyoda (JP)

(73) Assignee: Surpass Industry Co., Ltd., Gyoda (JP)

( * ) Notice: Subject to any disclaimer, the term of this patent is extended or adjusted under 35 U.S.C. 154(b) by 0 days.

(21) Appl. No.: 18/178,704

(22) Filed: Mar. 6, 2023

(65) Prior Publication Data

US 2023/0279975 A1  Sep. 7, 2023

(30) Foreign Application Priority Data

Mar. 7, 2022 (JP) ................................. 2022-034455

(51) Int. Cl.
*F16L 19/02* (2006.01)
*F16L 25/00* (2006.01)
*F16L 25/14* (2006.01)

(52) U.S. Cl.
CPC ....... *F16L 19/0206* (2013.01); *F16L 25/0018* (2013.01); *F16L 25/14* (2013.01)

(58) Field of Classification Search
CPC ... F16L 19/0206; F16L 19/0656; F16L 19/06; F16L 33/222; A61M 2039/1033
See application file for complete search history.

(56) References Cited

U.S. PATENT DOCUMENTS

| | | | | |
|---|---|---|---|---|
| 713,117 A | * | 11/1902 | Lee | F16L 33/222 285/243 |
| 1,181,676 A | * | 5/1916 | Lambkin | F16L 33/222 285/259 |
| 2,423,632 A | * | 7/1947 | Ansorge | F16L 33/222 285/259 |
| 4,162,802 A | * | 7/1979 | Cox | F16L 19/10 285/382.7 |

(Continued)

FOREIGN PATENT DOCUMENTS

| | | |
|---|---|---|
| JP | 2021050770 A | 4/2021 |
| JP | 2021055815 A | 4/2021 |

OTHER PUBLICATIONS

Extended European Search Report received for EP Application No. 23159880.6, dated Jul. 3, 2023, 8 pages.

*Primary Examiner* — David Bochna
(74) *Attorney, Agent, or Firm* — AEON Law, PLLC; Adam L. K. Philipp; James Namiki

(57) ABSTRACT

Provided is joint unit having a resin tube, a joint structure, and a nut, the joint structure has a guide part that guides the outer circumferential face of the resin tube, a protrusion that forms an insertion groove between the guide part and the protrusion, and a fixing part that fixes the resin tube inserted in the insertion groove, the tip of the protrusion is located closer to a main body than the tip of the guide part, the nut has a recessed part having an inner diameter greater than a first outer diameter of the guide part and smaller than a second outer diameter of the fixing part, and the tip of the fixing part in contact with the recessed part bites into the outer circumferential face of the resin tube in a state where the nut is fastened to the joint structure.

10 Claims, 12 Drawing Sheets

(56) References Cited

U.S. PATENT DOCUMENTS

| | | | | |
|---|---|---|---|---|
| 4,900,068 A | * | 2/1990 | Law | F16L 33/224 |
| | | | | 285/139.2 |
| 5,072,072 A | | 12/1991 | Bawa et al. | |
| 5,405,172 A | * | 4/1995 | Mullen, Jr. | F16L 19/0656 |
| | | | | 285/343 |
| 5,797,633 A | * | 8/1998 | Katzer | F16L 33/224 |
| | | | | 285/322 |
| 6,467,816 B1 | * | 10/2002 | Huang | F16L 19/0656 |
| | | | | 285/308 |
| 8,157,294 B2 | * | 4/2012 | Sisk | A61H 33/6063 |
| | | | | 285/243 |
| 9,601,914 B2 | * | 3/2017 | Chiu | H02G 15/007 |
| 9,784,389 B2 | * | 10/2017 | Fukano | F16L 19/0283 |
| 2004/0100097 A1 | | 5/2004 | Fukano et al. | |
| 2009/0174154 A1 | * | 7/2009 | Chiu | F16L 19/065 |
| | | | | 277/603 |
| 2021/0102649 A1 | | 4/2021 | Imai et al. | |

* cited by examiner

JOINT UNIT AND METHOD FOR ASSEMBLING JOINT UNIT

CROSS-REFERENCE TO RELATED APPLICATIONS

This application is based on Japanese Patent Application No. 2022-034455 filed on Mar. 7, 2022, the contents of which are incorporated herein by reference in its entirety.

BACKGROUND

1. Technical Field

The present disclosure relates to a joint unit and a method for assembling the joint unit.

2. Description of Related Art

Heretofore, in a use application to culture of cells for use in regenerative medicine, in a case where a liquid is allowed to flow into a tube, a flow rate may be required to be an extremely micro flow rate (e.g., from about 0.01 ml/min to 1 ml/min). The tube for such an application use has an extremely small inner diameter of a channel (e.g., about 0.30 mm). Furthermore, in a case of coupling the tube for use in the tube pump to another channel, a joint structure comprising a joint part to be partially inserted in the channel of the tube is required to couple these channels.

However, in a case where the inner diameter of the channel is smaller than the thickness of the tube, an operation of elastically deforming the channel of the tube having high rigidity and inserting the joint part in the channel is difficult. In particular, in a case where the inner diameter of the channel is extremely small, an operation of inserting the joint part while visually recognizing the channel is difficult.

Japanese Patent Application Laid-Open No. 2021-55815 discloses that a joint structure has a protrusion in a cylindrical part that holds the outer circumferential face of a resin tube, an insertion groove in which the resin tube is inserted is formed between the protrusion and the cylindrical part, and the tip of the protrusion is located closer to the main body than the tip of the cylindrical part. Before the end of the resin tube comes into contact with the tip of the protrusion, the outer circumferential face of the resin tube is held in the inner circumferential face of the cylindrical part. The outer circumferential face of the resin tube is held by the inner circumferential face of the cylindrical part, and thereby a liquid transferring channel formed in the resin tube is arranged on the same axis as the center axis of the cylindrical part.

When an operator pushes the resin tube against the main body of the joint structure in this state, the protrusion arranged on the same axis is inserted in the liquid transferring channel. In such a way, according to Japanese Patent Application Laid-Open No. 2021-55815, the operator is able to easily perform an operation to insert the protrusion in the liquid transferring channel without visually checking the liquid transferring channel formed in the resin tube. In Japanese Patent Application Laid-Open No. 2021-55815, the resin tube is fixed by an adhesive agent or a ferrule so that the resin tube does not come off of the protrusion.

BRIEF SUMMARY

When the resin tube is fixed to the joint structure by an adhesive agent, however, since the resin tube is adhered to the joint structure, it is not possible to replace the resin tube to reuse the joint structure. Further, when the resin tube is fixed to the joint structure by a ferrule, this limits the amount of deformation of the ferrule formed in a cylindrical shape. This may lead to a case where sufficient holding force for fixing the resin tube so that the resin tube does not come off of the protrusion is not exerted. Further, since the ferrule is a different member from the joint structure, the operator may forget to mount the ferrule. In such a case, the resin tube may come off of the protrusion.

The present disclosure has been made in view of such circumstances, and an object is to provide a joint unit and a method for assembling a joint unit that enable an operator to easily perform an operation to insert a protrusion in a liquid transferring channel of a resin tube and can reliably exert sufficient holding force for fixing the resin tube so that the resin tube does not come off of the protrusion.

To achieve the above object, the present disclosure employs the following solutions.

A joint unit according to one aspect of the present disclosure has: a resin tube in which a liquid transferring channel extending along an axis is formed and whose cross section orthogonal to the axis is circular; a joint structure formed in a shaft shape along the axis, having an external thread in an outer circumferential face of the joint structure, and configured to be attached to an end of the resin tube; and a nut formed in a cylindrical shape along the axis and having an internal thread formed in an inner circumferential face of the nut, the internal thread being configured to be engaged with the external thread. The joint structure includes a main body, at least one guide part formed in a part in a circumferential direction about the axis so as to protrude along the axis from the main body and configured to guide an outer circumferential face of the resin tube, a protrusion formed in a shaft shape so as to protrude along the axis from the main body and forming an insertion groove between the guide part and the protrusion, the resin tube being inserted in the insertion groove, and at least one fixing part formed in a part in the circumferential direction so as to protrude along the axis from the main body and configured to fix the resin tube inserted in the insertion groove, a coupling channel extending along the axis and configured to couple the liquid transferring channel and another channel is formed in the main body and the protrusion, a tip of the protrusion is located closer to the main body than a tip of the guide part, the nut has a recessed part having an inner diameter that is larger than a first outer diameter of the guide part and smaller than a second outer diameter of the fixing part, and a tip of the fixing part in contact with the recessed part bites into the outer circumferential face of the resin tube in a state where the nut is fastened to the joint structure.

According to the joint unit of one aspect of the present disclosure, the joint unit has the protrusion, the insertion groove in which the resin tube is inserted is formed between the protrusion and the guide part that guides the outer circumferential face of the resin tube, and the tip of the protrusion is located closer to the main body than the tip of the guide part. Thus, when the end of the resin tube is moved closer to the joint structure, the outer circumferential face of the resin tube is guided by the inner circumferential face of the guide part before the end of the resin tube comes into contact with the tip of the protrusion. Once the outer circumferential face of the resin tube is guided to the inner circumferential face of the guide part, the liquid transferring channel formed in the resin tube is arranged on the same axis as the center axis of the protrusion.

When the operator pushes the resin tube against the main body of the joint structure in this state, the protrusion arranged on the same axis is inserted in the liquid transferring channel. In such a way, the operator is able to easily perform an operation to insert the protrusion in the liquid transferring channel without visually checking the liquid transferring channel formed in the resin tube.

Further, according to the joint unit of one aspect of the present disclosure, the nut has the recessed part having the inner diameter that is larger than the first outer diameter of the guide part and smaller than the second outer diameter of the fixing part. Since the inner diameter of the recessed part is larger than the first outer diameter of the guide part, the guide part is secured in the recessed part without the guide part coming into contact with the inner circumferential face of the recessed part when the nut is fastened to the joint structure. On the other hand, since the inner diameter of the recessed part is smaller than the second outer diameter of the fixing part, the fixing part comes into contact with the inner circumferential face of the recessed part when the nut is fastened to the joint structure. The tip of the fixing part in contact with the recessed part then bites into the outer circumferential face of the resin tube in a state where the nut is fastened to the joint structure. This is because, due to the tip of the fixing part coming into contact with the recessed part, the fixing part, which is formed in only a part in the circumferential direction, is easily deformed toward the inner circumferential side. In such a way, by causing the tip of the fixing part to bite into the outer circumferential face of the resin tube, it is possible to reliably exert sufficient holding force for fixing the resin tube so that the resin tube does not come off of the protrusion.

In the joint unit according to one aspect of the present disclosure, a preferred configuration is such that the joint structure has a plurality of guide parts arranged spaced apart by intervals in the circumferential direction and a plurality of fixing parts arranged spaced apart by intervals in the circumferential direction, and the fixing parts are arranged between a pair of the guide parts arranged adjacent to each other.

According to the joint unit of the present configuration, with the use of the plurality of guide parts arranged spaced apart by intervals in the circumferential direction, it is possible to reliably guide the outer circumferential face of the resin tube and arrange the liquid transferring channel on the same axis as the center axis of the protrusion. Further, the plurality of fixing parts, which are arranged between the pair of guide parts arranged adjacent to each other, are arranged spaced apart by intervals in the circumferential direction, and this makes it possible to reliably exert sufficient holding force for fixing the resin tube so that the resin tube does not come off of the protrusion.

In the joint unit according to one aspect of the present disclosure, a preferred configuration is such that the recessed part has a bottom against which the tip of the guide part is abutted.

According to the joint unit of the present configuration, when fastening the nut to the joint structure, because the tip of the guide part is abutted to the bottom of the recessed part, the operator is able to easily recognize that the nut has been fastened to the joint structure, and this makes it possible to prevent the nut from being excessively clamped to the joint structure.

In the joint unit according to one aspect of the present disclosure, a preferred configuration is such that the tip of the fixing part is located closer to the main body than the tip of the protrusion.

According to the joint unit of the present configuration, the force exerted when the tip of the fixing part is caused to bite into the outer circumferential face of the resin tube is not exerted on a region that is more distant from the main body than the tip of the protrusion. It is thus possible to prevent a failure of blockage of the liquid transferring channel resulted from that the resin tube is deformed by the force exerted when the tip of the fixing part is caused to bite into the outer circumferential face of the resin tube.

In the joint unit according to one aspect of the present disclosure, a preferred configuration is such that a biting part protruding toward the protrusion in a radial direction orthogonal to the axis and configured to bite into the outer circumferential face of the resin tube is formed at the tip of the fixing part.

According to the joint unit of the present configuration, by causing the biting part protruding toward the protrusion in the radial direction to bite into the outer circumferential face of the resin tube, it is possible to reliably exert sufficient holding force for fixing the resin tube so that the resin tube does not come off of the protrusion.

In the joint unit according to an aspect of the present disclosure, a preferred configuration is such that a length of the protrusion along the axis is three times or more as large as an outer diameter of the protrusion.

According to the joint unit of the present configuration, since the length of the protrusion along the axis is three times or more as large as the outer diameter of the protrusion, the protrusion has a needle-like shape that protrudes from the main body. When the needle-like protrusion is inserted in the liquid transferring channel of the resin-made tube, a seal region having a sufficient length can be provided between an outer peripheral surface of the protrusion and the liquid transferring channel. Furthermore, it is a difficult operation for the operator to insert the needle-like protrusion in the liquid transferring channel while visually recognizing the protrusion. However, the protrusion is inserted in the liquid transferring channel in a state where the liquid transferring channel and the protrusion are arranged on the same axis, and hence the operator can easily perform the operation of inserting the protrusion in the liquid transferring channel.

In the joint unit according to an aspect of the present disclosure, a preferred configuration is such that a length from the tip of the protrusion to the tip of the guide part is 0.2 times or more as large as an inner diameter of the guide part.

According to the joint unit of the present configuration, since the length from the tip of the protrusion to the tip of the guide part is 0.2 times or more as large as the inner diameter of the tubular part. Therefore, the end of the resin-made tube comes in contact with the tip of the protrusion in a state where the end of the resin-made tube is inserted as much as the sufficient length relative to the inner diameter of the guide part. Consequently, the operation of inserting the protrusion in the liquid transferring channel can be performed in a state where the outer peripheral surface of the resin-made tube is securely held by the inner peripheral surface of the guide part.

In the joint unit according to an aspect of the present disclosure, a preferred configuration is such that the outer diameter of the resin-made tube is three times or more and 15 times or less as large as an inner diameter of the resin-made tube.

According to the joint unit of the present configuration, since the outer diameter of the resin-made tube is sufficiently larger than the inner diameter thereof, the resin-made tube is provided with a sufficient thickness. Therefore, for example, also in a case where durability to a pressing force is required as in use in a tube pump, sufficient rigidity and corresponding durability can be exerted. Furthermore, in a case of using the resin-made tube having high rigidity, it is difficult to insert the protrusion for the elastic deformation. However, it is possible to perform an operation of inserting the protrusion in the liquid transferring channel in a state where the outer peripheral surface of the resin-made tube is held by the inner peripheral surface of the guide part, and hence the protrusion can be easily inserted in the resin-made tube.

In the joint unit according to an aspect of the present disclosure, a preferred configuration is such that the inner diameter of the resin-made tube is 0.1 mm or more and 1.0 mm or less.

According to the joint unit of the present configuration, since the inner diameter of the resin-made tube is an extremely small diameter of 0.1 mm or more and 1.0 mm or less, a flow rate of a liquid flowing through the channel formed in the resin-made tube per unit time can be maintained to be small. Furthermore, even if the inner diameter of the resin-made tube is the extremely small diameter of 0.1 mm or more and 1.0 mm or less, the operation of inserting the protrusion in the liquid transferring channel can be easily performed without visually recognizing the liquid transferring channel formed in the resin-made tube.

A method for assembling a joint unit according to one aspect of the present disclosure is a method of assembling a resin tube in which a liquid transferring channel extending along an axis is formed and whose cross section orthogonal to the axis is circular and a joint unit attached to the end of the resin tube. The joint unit has a joint structure formed in a shaft shape along the axis and having an external thread formed in an outer circumferential face of the joint structure and a nut formed in a cylindrical shape along the axis and having an internal thread formed in an inner circumferential face of the nut and configured to be engaged with the external thread. The joint structure has a main body, a guide part formed so as to protrude along the axis from the main body and configured to guide an outer circumferential face of the resin tube, a protrusion formed in a shaft shape so as to protrude along the axis from the main body and forming an insertion groove between the guide part and the protrusion, the resin tube being inserted in the insertion groove, and a fixing part formed so as to protrude along the axis from the main body and configured to fix the resin tube inserted in the insertion groove, a coupling channel extending along the axis and configured to couple the liquid transferring channel and another channel is formed in the main body and the protrusion, a tip of the protrusion is located closer to the main body than a tip of the guide part, and the nut has a recessed part having an inner diameter that is larger than a first outer diameter of the guide part and smaller than a second outer diameter of the fixing part. The method includes: an insertion step of guiding the outer circumferential face of the resin tube by the guide part and inserting the protrusion in the liquid transferring channel; and a fixing step of fastening the nut to the joint structure to cause the fixing part to come into contact with the recessed part and cause the tip of the fixing part to bite into the outer circumferential face of the resin tube.

According to the method for assembling a joint unit of one aspect of the present disclosure, in the insertion step, the outer circumferential face of the resin tube is guided by the inner circumferential face of the guide part before the end of the resin tube comes into contact with the tip of the protrusion. When the operator pushes the resin tube against the main body of the joint structure in this state, the protrusion arranged on the same axis is inserted in the liquid transferring channel. In such a way, the operator is able to easily perform an operation to insert the protrusion in the liquid transferring channel without visually checking the liquid transferring channel formed in the resin tube.

Further, according to the method for assembling a joint unit of one aspect of the present disclosure, the inner diameter of the recessed part is smaller than the second outer diameter of the fixing part, and thus, in the fixing step, the fixing part comes into contact with the inner circumferential face of the recessed part when the nut is fastened to the joint structure. The tip of the fixing part in contact with the recessed part then bites into the outer circumferential face of the resin tube in a state where the nut is fastened to the joint structure. This is because, due to the tip of the fixing part coming into contact with the recessed part, the fixing part formed in only a part in the circumferential direction is easily deformed toward the inner circumferential side. In such a way, by causing the tip of the fixing part to bite into the outer circumferential face of the resin tube, it is possible to reliably exert sufficient holding force for fixing the resin tube so that the resin tube does not come off of the protrusion.

According to the present disclosure, it is possible to provide a joint unit and a method for assembling a joint unit that enables an operator to easily perform an operation to insert a protrusion in a liquid transferring channel of a resin tube and can reliably exert sufficient holding force for fixing the resin tube so that the resin tube does not come off of the protrusion.

BRIEF DESCRIPTION OF THE SEVERAL
VIEWS OF THE DRAWINGS

DETAILED DESCRIPTION

Figure 1:
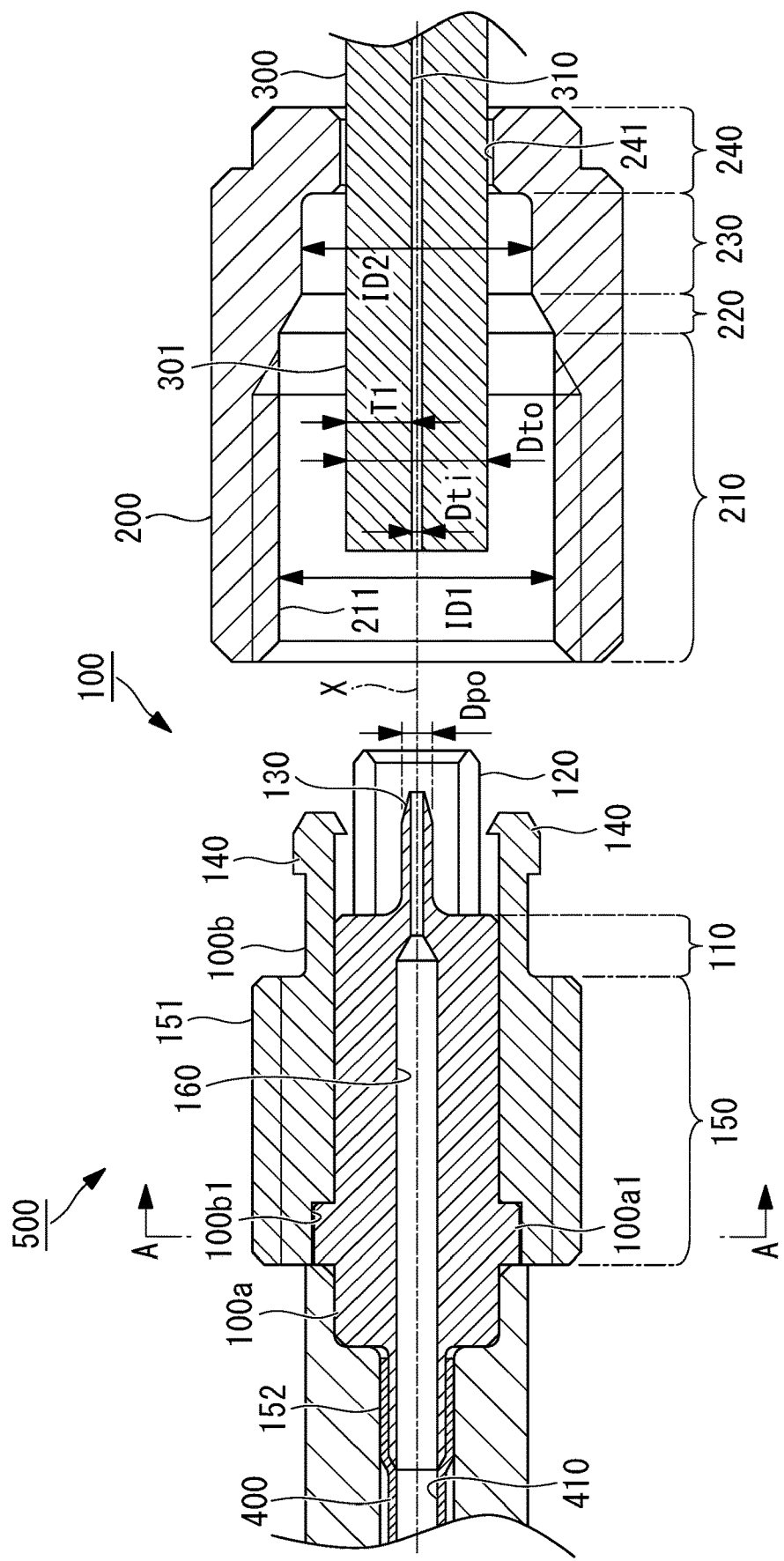
FIG. 1 is a longitudinal sectional view illustrating a joint unit according to one embodiment of the present disclosure and illustrates a state before a resin tube is inserted in a joint structure.
Figure 2:
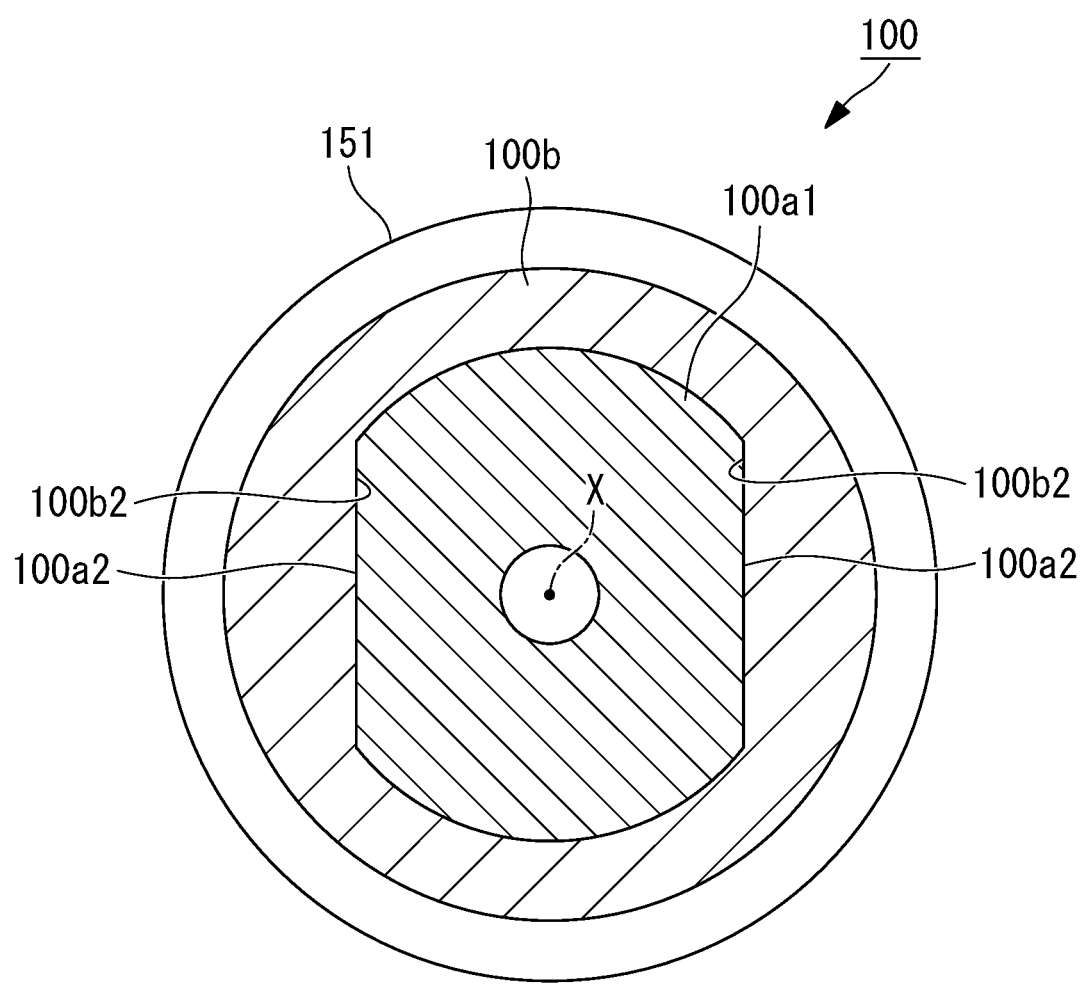
FIG. 2 is a sectional view taken along an arrow A-A of the joint structure illustrated in FIG. 1.
Figure 3:
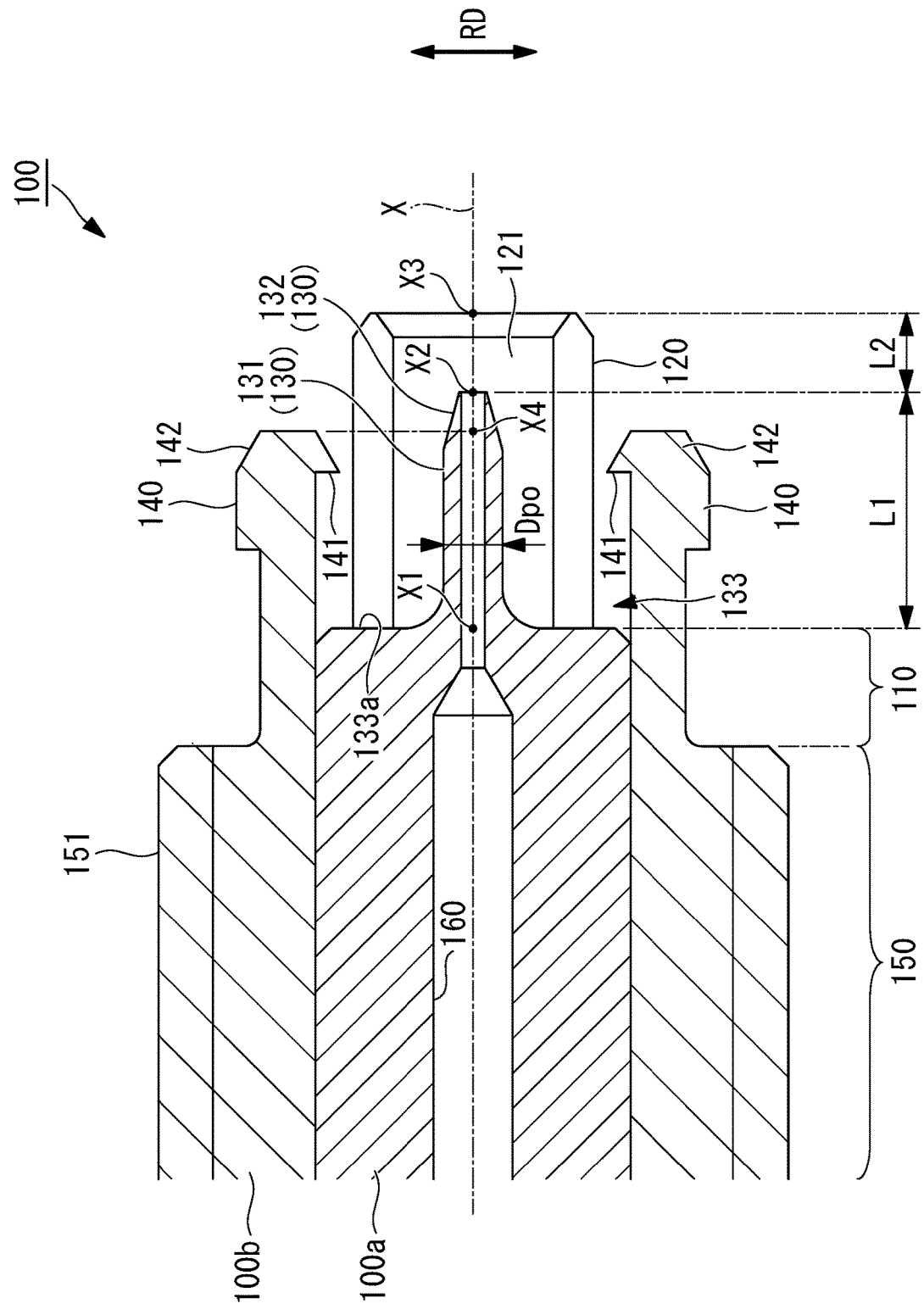
FIG. 3 is a partial enlarged view of the joint structure illustrated in FIG. 1.
Figure 4:
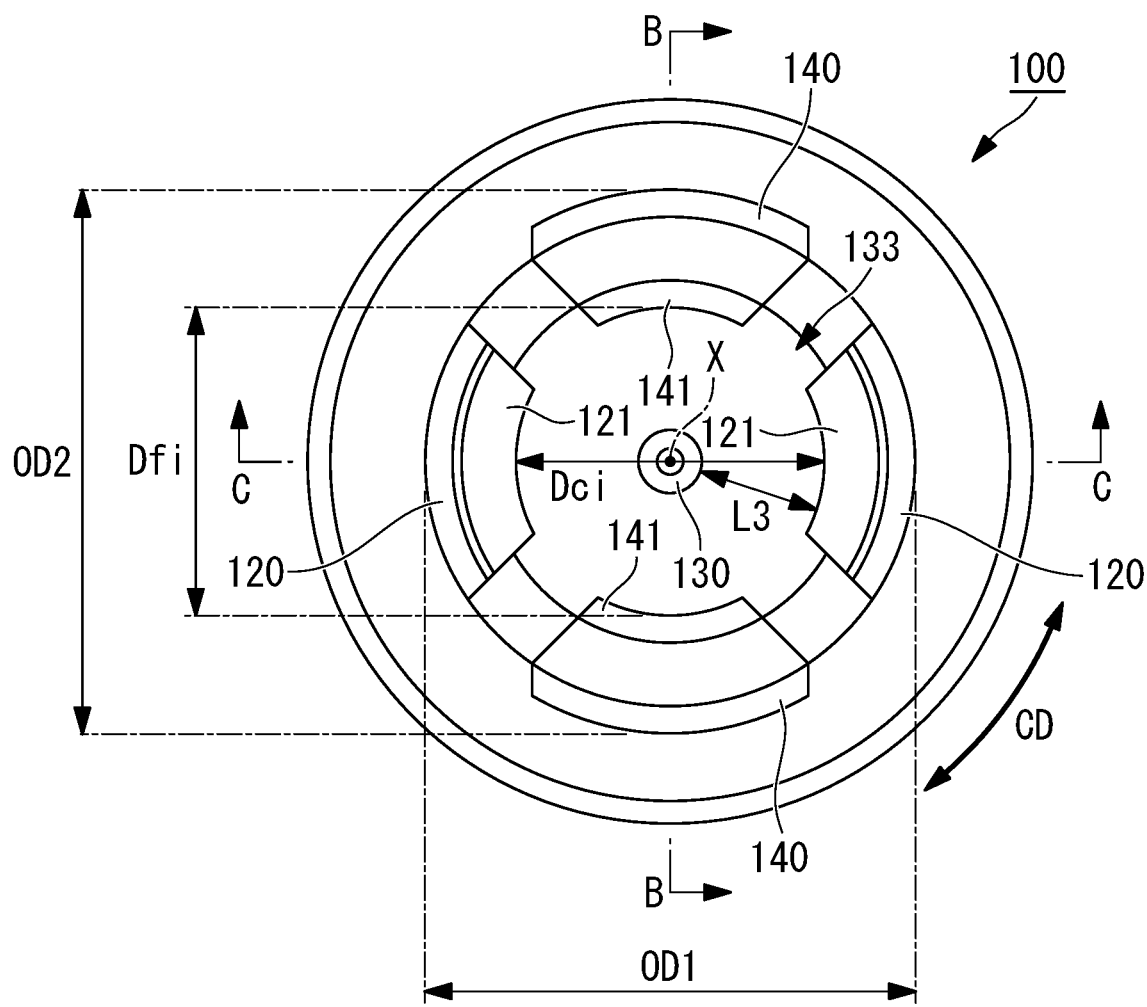
FIG. 4 is a side view of the joint structure illustrated in FIG. 1 when viewed from the resin tube side.

A joint unit 500 of one embodiment of the present disclosure will be described below with reference to the drawings. FIG. 1 is a longitudinal sectional view illustrating the joint unit 500 according to one embodiment of the present disclosure and illustrates a state before a resin tube 300 is inserted in a joint structure 100. FIG. 2 is a sectional view taken along the arrow A-A of the joint structure 100 illustrated in FIG. 1. FIG. 3 is a partial enlarged view of the joint structure 100 illustrated in FIG. 1. FIG. 4 is a side view of the joint structure 100 illustrated in FIG. 1 when viewed from the resin tube 300 side.

As illustrated in FIG. 1, the joint unit 500 of the present embodiment has the joint structure 100, a nut 200, the resin tube 300, and a resin tube 400.

The joint structure 100 is a structure to which the end of the resin tube 300 is attached at one end side (the right side in FIG. 1) and the end of the resin tube 400 is attached at the other end side (the left side in FIG. 1). The joint structure 100 couples a liquid transferring channel 310 of the resin tube 300 and a liquid transferring channel 410 of the resin tube 400 to each other so that a liquid flows through these channels.

The joint structure 100 is a member formed in a shaft shape along an axis X and formed of a first member 100a and a second member 100b coupled to each other. The first member 100a is a member formed in a shaft shape along the axis X. The second member 100b is a member formed in a cylindrical shape along the axis X. Each of the first member 100a and the second member 100b is made of a resin material (for example, polyvinyl chloride (PVC), polycarbonate).

As illustrated in FIG. 1, the first member 100a has an engaging part 100a1 that engages with an end on the resin tube 400 side of the second member 100b. As illustrated in FIG. 2, a pair of flat faces 100a2 at positions facing each other via the axis X are formed in the engaging part 100a1. As illustrated in FIG. 1, the second member 100b has a holding part 100b1 that holds the engaging part 100a1 of the first member 100a. As illustrated in FIG. 2, a pair of flat faces 100b2 at positions facing each other via the axis X are formed in the holding part 100b1.

As illustrated in FIG. 2, the first member 100a is inserted in the second member 100b so that the pair of flat faces 100a2 face the pair of flat faces 100b2. Since the pair of flat faces 100a2 face the pair of flat faces 100b2, the first member 100a is fixed so as not to be rotated about the axis X relative to the second member 100b. The first member 100a and the second member 100b are joined to each other by a UV curable adhesive agent, for example.

As illustrated FIG. 1, the joint structure 100 has a main body 110, guide parts 120, a protrusion 130, fixing parts 140, and an external thread part 150. A coupling channel 160 extending along the axis X and configured to couple the liquid transferring channel 310 of the resin tube 300 and the liquid transferring channel 410 of the resin tube 400 to each other is formed in the main body 110, the protrusion 130, and the external thread part 150.

The main body 110 is arranged between the protrusion 130 and the external thread part 150, and the coupling channel 160 is formed inside the main body 110.

Each guide part 120 is formed so as to protrude along the axis X from the main body 110 to the resin tube 300 side. As illustrated in FIG. 4, the guide part 120 is formed in a part in the circumferential direction CD about the axis X. The joint structure 100 has two guide parts 120 arranged spaced apart from each other by intervals of 180 degrees in the circumferential direction. The guide part 120 has an arc-shaped inner circumferential face 121 that guides the outer circumferential face 301 of the resin tube 300. The outer diameter of the pair of guide parts 120 is OD1.

The protrusion 130 is formed in a shaft shape to protrude from the main body 110 along the axis X to the resin-made tube 300 side. As shown in FIG. 3, the protrusion 130 includes a base 131 having an outer diameter Dpo, and a tip portion 132 having an outer diameter that gradually decreases toward a tip. The protrusion 130 forms, between the guide part 120 and the fixing parts 140, an insertion groove 133 in which the resin-made tube 300 is inserted. A bottom 133a of the insertion groove 133 corresponds to a boundary position between the main body 110 and the protrusion 130.

As shown in FIG. 3, a boundary position between the main body 110 and the protrusion 130 on the axis X is denoted with X1, a position of a tip of the protrusion 130 on the axis X is denoted with X2, and a position of a tip of the guide part 120 on the axis X is denoted with X3. The position X2 of the tip of the protrusion 130 is disposed closer to the position X1 of an end of the main body 110 on a protrusion 130 side than the position X3 of the tip of the guide part 120.

As shown in FIG. 3, a length L2 from the tip of the protrusion 130 to the tip of the guide part 120 is the length L2 from X2 to X3 in an axis X direction. As shown in FIG. 4, an inner diameter of a pair of the guide part 120 is denoted with Dci. It is preferable that the length L2 from the tip of the protrusion 130 to the tip of the guide part 120 is 0.2 times or more as large as the inner diameter Dci of the pair of the guide part 120.

Since the length L2 is 0.2 times or more as large as the inner diameter Dci, the end of the resin-made tube 300 comes in contact with the tip of the protrusion 130 in a state where the end of the resin-made tube 200 is inserted as much as the sufficient length L2 relative to the inner diameter Dci of the pair of the guide part 120. Consequently, the operation of inserting the protrusion 130 in the liquid transferring channel 310 can be performed in a state where the outer peripheral surface of the resin-made tube 300 is securely held by the inner peripheral surface of the guide part 120.

As shown in FIG. 3, a length of the protrusion 130 along the axis X is a length L1 from X1 to X2 in the axis X direction. Furthermore, the outer diameter of the protrusion 130 is denoted with Dpo. It is preferable that the length L1 of the protrusion 130 is three times or more as large as the outer diameter Dpo of the protrusion 130. In a case where the length L1 of the protrusion 130 is three times or more as large as the outer diameter Dpo of the protrusion 130, the protrusion 130 has a needle-like shape that protrudes from the main body 110. When the needle-like protrusion 130 is inserted in the liquid transferring channel 310 of the resin-made tube 300, a seal region having a sufficient length can be provided between an outer peripheral surface of the protrusion 130 and the liquid transferring channel 310.

Each fixing part 140 is a member that fixes the resin tube 300 inserted in the insertion groove 133. As illustrated in FIG. 3, a biting part 141 protruding toward the protrusion 130 in the radial direction RD orthogonal to the axis X is formed at the tip of the fixing part 140. The biting part 141 is a member that bites into the outer circumferential face 301 of the resin tube 300 in a state where the nut 200 is fastened to the joint structure 100.

As illustrated in FIG. 4, the fixing part 140 is formed in a part in the circumferential direction CD so as to protrude along the axis X from the main body 110. The joint structure 100 has two fixing parts 140 arranged space away from each other by intervals of 180 degrees in the circumferential direction CD. Each fixing part 140 is arranged between the pair of guide parts 120 arranged adjacent to the fixing part 140. The guide parts 120 and the fixing parts 140 are arranged alternatingly in the circumferential direction CD.

In the joint structure 100 of the present embodiment, the length in the circumferential direction CD of the guide part 120 and the length in the circumferential direction CD of the fixing part 140 may be the same. Further, in the joint structure 100 of the present embodiment, the length in the circumferential direction CD of the guide part 120 and the length in the circumferential direction CD of the fixing part 140 may differ from each other. In the joint structure 100 of the present embodiment, it is preferable that the length in the circumferential direction CD of the guide part 120 be longer than the length in the circumferential direction CD of the fixing part 140. By setting the length in the circumferential direction CD of the guide part 120 to be longer than the length in the circumferential direction CD of the fixing part 140, it is possible to achieve a state where the outer circumferential face 301 of the resin tube 300 is reliably held by the inner circumferential face of the guide part 120.

As illustrated in FIG. 3, the position on the axis X of the tip of the fixing part 140 is X4. The position X4, which is the tip of the fixing part 140, is located closer to the position X1, which is the position of the end of the main body 110 on the protrusion 130 side, than the position X2, which is the tip of the protrusion 130. The outer diameter of the pair of fixing parts 140 is OD2 and is larger than the outer diameter OD1 of the pair of guide parts 120.

The external thread part 150 is a member adjacent to the main body 110 and extending in a shaft-like manner along the axis X. The external thread 151 is formed in the outer circumferential face of the external thread part 150. A connection part 152 to which the end of the resin tube 400 is connected is formed at an end of the external thread part 150 on the resin tube 400 side along the axis X.

The nut 200 is a member removably attached to the external thread part 150 of the joint structure 100. The nut 200 causes the tips of the fixing parts 140 to bite into the outer circumferential face 301 of the resin tube 300 in a fastened state where the nut 200 is fastened to the joint structure 100. As illustrated in FIG. 1, the nut 200 has an internal thread part 210, a coupling part 220, a recessed part 230, and a base end 240 in this order from the joint structure 100 side.

The internal thread part 210 is formed in a cylindrical shape along the axis X, and an internal thread 211 is formed in the inner circumferential face. The operator attaches the nut 200 to the joint structure 100 by engaging the internal thread 211 with the external thread 151 while rotating the nut 200 about the axis X. The inner diameter of the internal thread part 210 is ID1.

The coupling part 220 is a member that couples the internal thread part 210 and the recessed part 230 to each other. The coupling part 220 has a shape whose inner diameter gradually decreases at a constant slope from ID1 to ID2 from the internal thread part 210 toward the recessed part 230. The coupling part 220 functions as an abutment face to deform the tips of the fixing parts 140 to come closer to the axis X when the tips of the fixing parts 140 of the joint structure 100 come into contact with the coupling part 220.

The recessed part 230 is a member formed in a cylindrical shape along the axis X. The recessed part 230 has a constant inner diameter ID2 from the coupling part 220 to the base end 240. The inner diameter ID2 of the recessed part 230 is larger than the outer diameter OD1 of the pair of guide parts 120 and smaller than the outer diameter OD2 of the pair of fixing parts 140.

The reason for the inner diameter ID2 of the recessed part 230 being larger than the outer diameter OD1 of the pair of guide parts 120 is not to cause the recessed part 230 to come into contact with the guide parts 120 in a state where the nut 200 is fastened to the joint structure 100. The reason for the inner diameter ID2 of the recessed part 230 being smaller than the outer diameter OD2 of the pair of fixing parts 140 is not to cause the recessed part 230 to come into contact with the guide parts 120 in a state where the nut 200 is fastened to the joint structure 100.

The base end 240 is a member formed in a cylindrical shape along the axis X, and a through hole 241 for inserting the resin tube 300 therein is formed in the base end 240. The resin tube 300 is a tube body inside which a liquid transferring channel 310 extending along the axis X is formed and whose cross section orthogonal to the axis X is circular. The resin tube 300 is made of a resin material such as polyvinyl chloride (PVC), silicone, pharmed, or the like, for example. The resin tube 300 is attached to the protrusion 130 arranged at the end of the joint structure 100.

As illustrated in FIG. 1, in a non-insertion state where the protrusion 130 of the joint structure 100 is not inserted in the liquid transferring channel 310 of the resin tube 300, the outer diameter Dpo of the protrusion 130 is larger than the inner diameter Dti of the liquid transferring channel 310. Further, the outer diameter Dto of the resin tube 300 is smaller than the inner diameter Dci of the guide parts 120 (see FIG. 4) and is smaller than the inner diameter Dfi of the pair of fixing parts 140 (see FIG. 4). The inner diameter Dfi is the distance between the pair of biting parts 141. For example, it is preferable that the inner diameter Dci and the inner diameter Dfi be smaller by about 0.1 mm than the outer diameter Dto of the resin tube 300.

It is preferable that the inner diameter Dci of the guide parts 120 and the inner diameter Dfi of the fixing parts 140 be the same or substantially the same. This can ensure the resin tube 300 to be guided so that the protrusion 130 is inserted in the liquid transferring channel 310 by the guide parts 120 and the fixing parts 140 having the same or substantially the same inner diameter.

A thickness T1 of the resin-made tube 300 is $(Dto-Dti)/2$. A distance L3 between an inner peripheral surface of the guide part 120 and the outer peripheral surface of the protrusion 130 is $(Dci-Dpo)/2$ (See FIG. 4). The thickness T1 of the resin-made tube 300 is equal to the distance L3, or slightly smaller than the distance L3. With such a relation, when the resin-made tube 300 is inserted in the protrusion 130, an outer peripheral surface 301 of the resin-made tube 300 is in contact with the inner peripheral surface of the guide part 120 or close to the inner peripheral surface via a minute space.

In the non-inserted state, the outer diameter Dto of the resin-made tube 300 is three times or more and 15 times or less as large as the inner diameter Dti. Furthermore, it is preferable that the outer diameter Dto of the resin-made tube 300 is seven times or more and eight times or less as large as the inner diameter Dti. Since the outer diameter Dto of the resin-made tube 300 is sufficiently larger than the inner diameter Dti, the resin-made tube 300 is provided with the sufficient thickness T1.

The inner diameter Dti of the resin-made tube 300 is 0.1 mm or more and 1.0 mm or less. Since the inner diameter Dti of the resin-made tube 300 is an extremely small diameter of 0.1 mm or more and 1.0 mm or less, a flow rate of a liquid flowing through the liquid transferring channel 310 formed in the resin-made tube 300 per unit time can be maintained to be small.

The resin-made tube 400 is a tubular body in which the liquid transferring channel 410 extending along the axis X is formed, and a cross section orthogonal to the axis X is round. The resin-made tube 400 is made of, for example, a resin material such as polyvinyl chloride (PVC), silicone, or PharMed (registered trademark). The resin-made tube 400 is attached to an outer peripheral surface of the connection part 152 formed in the end of the joint structure 100.

Next, description will be made as to an assembly method of the joint unit 500 of the present embodiment with reference to FIGS. 5-10. The assembly method of the joint unit 500 of the present embodiment includes attaching the end of the resin-made tube 300 to one end side (a right side of FIG. 1) of the joint structure 500.

Figure 5:
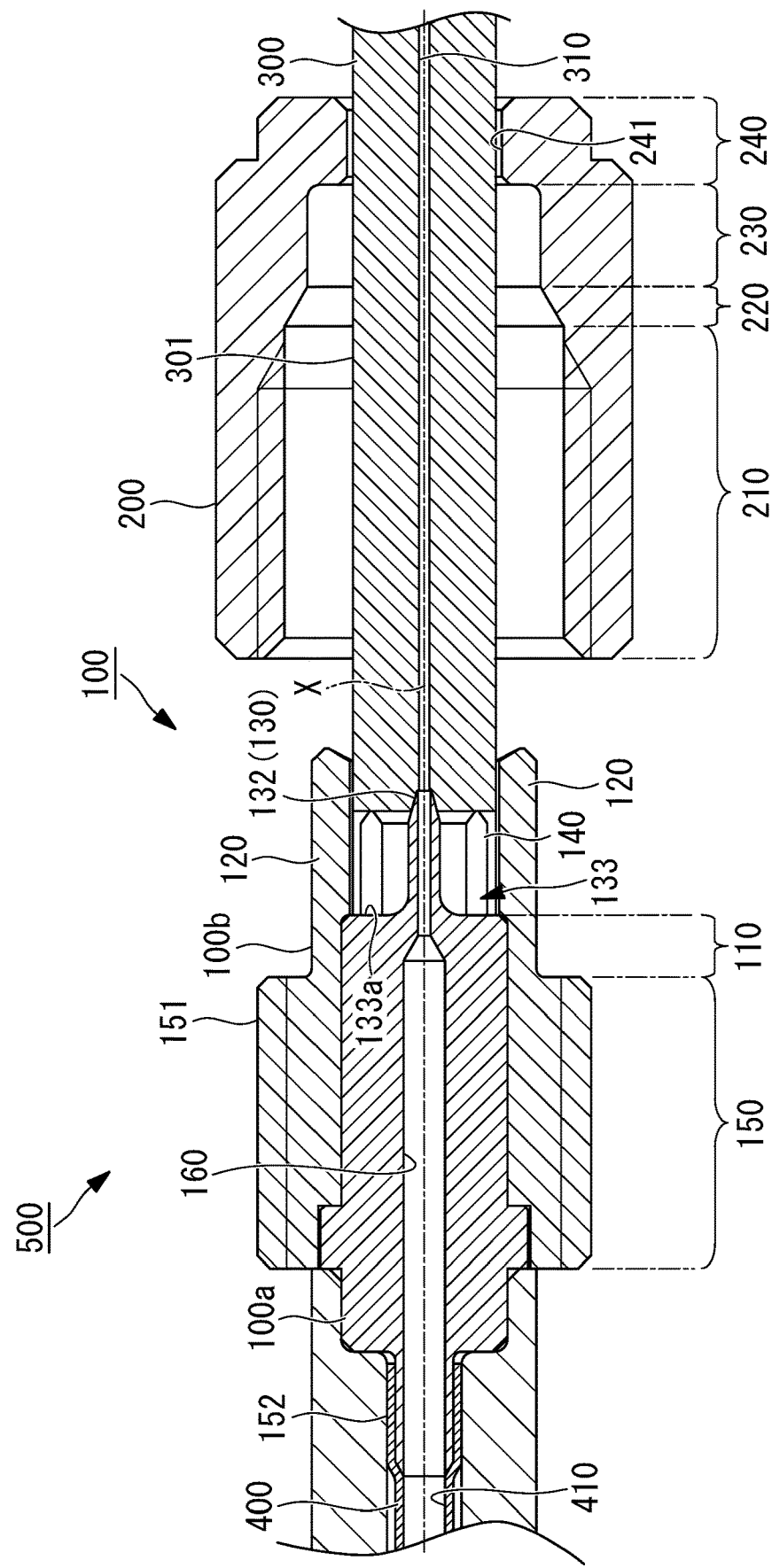
FIG. 5 is a sectional view taken along an arrow C-C of the joint structure illustrated in FIG. 4 and illustrates a state where the tip of a protrusion is inserted in a liquid transferring channel of the resin tube.

The operator inserts the end of the resin tube 300 in the through hole 241 of the nut 200 to have the state illustrated in FIG. 1. Next, the operator grips both the resin tube 300 and the joint structure 100 and inserts the end of the resin tube 300 in the inner circumferential side of the guide parts 120 of the joint structure 100 to have the state illustrated in FIG. 5. FIG. 5 is a sectional view taken along the arrow C-C of the joint structure 100 illustrated in FIG. 4 and illustrates a state where the tip of the protrusion 130 is inserted in the liquid transferring channel 310 of the resin tube 300.

As illustrated in FIG. 5, the end of the resin tube 300 comes into contact with the tip 132 of the protrusion 130 of the joint structure 100. In the state illustrated in FIG. 5, a state where the outer circumferential face 301 of the resin tube 300 is held by the inner circumferential face of the guide parts 120 is obtain. Therefore, even when the operator moves the resin tube 300 in a direction orthogonal to the axis X, the state where the outer circumferential face 301 of the resin tube 300 is in contact with the inner circumferential face of the guide parts 120 and is arranged on the inner circumferential side of the guide parts 120 will be maintained.

Figure 6:
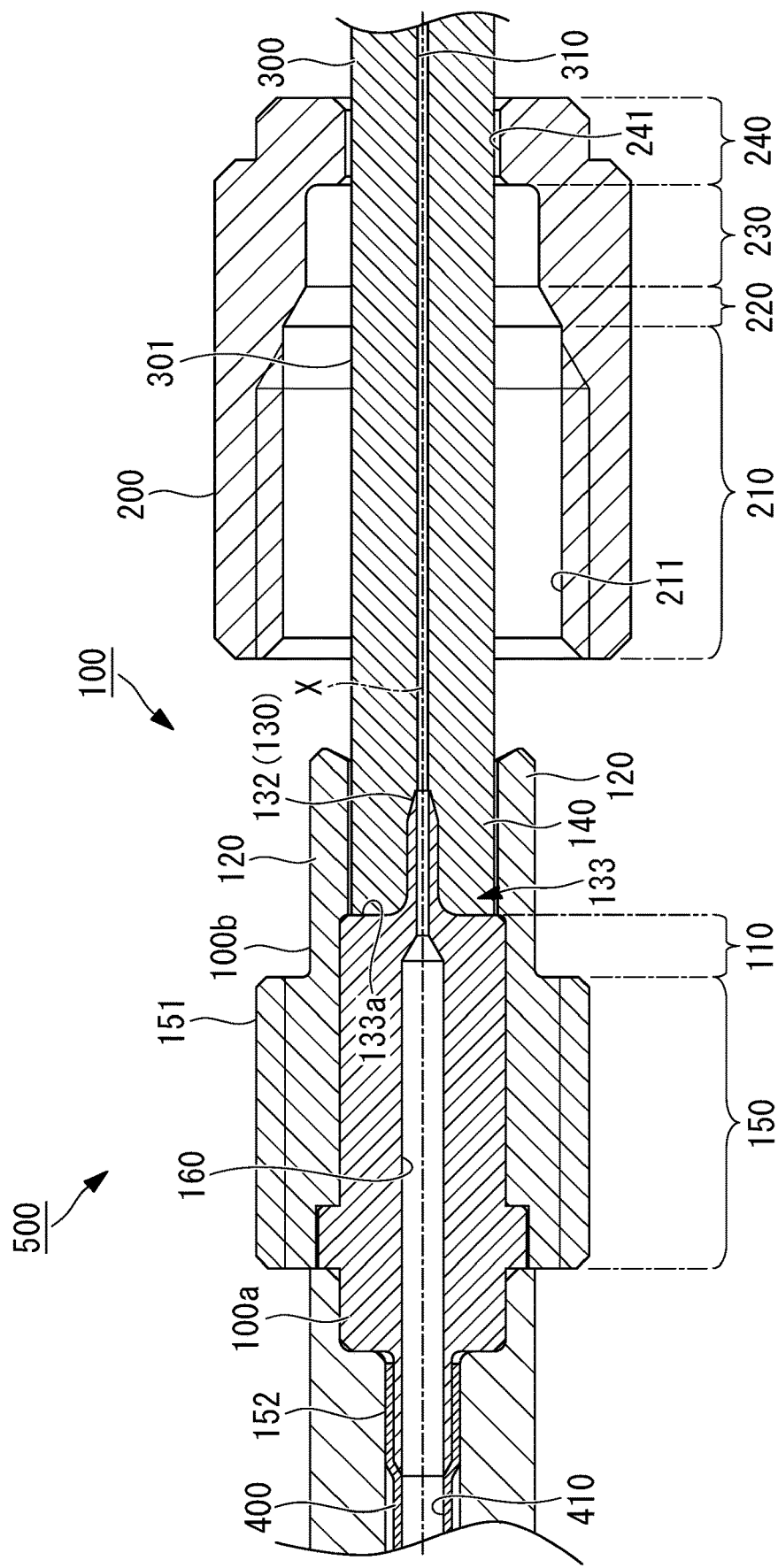
FIG. 6 is a sectional view taken along the arrow C-C of the joint structure illustrated in FIG. 4 and illustrates a state where insertion of the resin tube is completed.

Next, the operator pushes the end of the resin tube 300 against the bottom 133a of the insertion groove 133 while gripping both the resin tube 300 and the joint structure 100. As illustrated in FIG. 6, once the end of the resin tube 300 is pushed against the bottom 133a of the insertion groove 133, the protrusion 130 of the joint structure 100 is inserted in the liquid transferring channel 310 of the resin tube 300, and a state where the end of the resin tube 300 is in contact with the bottom 133a of the insertion groove 133 is obtained (insertion step). FIG. 6 is a sectional view taken along the arrow C-C of the joint structure 100 illustrated in FIG. 4 and illustrates a state where insertion of the resin tube 300 is completed.

If the guide parts 120 were absent when the end of the resin tube 300 is pushed against the bottom 133a of the insertion groove 133, the position of the tip 132 of the protrusion 130 may be out of the position of the liquid transferring channel 310 of the resin tube 300 due to the operator's operation when pushing the resin tube 300. In the present embodiment, the outer circumferential face 301 of the resin tube 300 is held by the inner circumferential face of the guide parts 120, and this prevents the position of the tip 132 of the protrusion 130 from being out of the position of the liquid transferring channel 310 of the resin tube 300.

Figure 7:
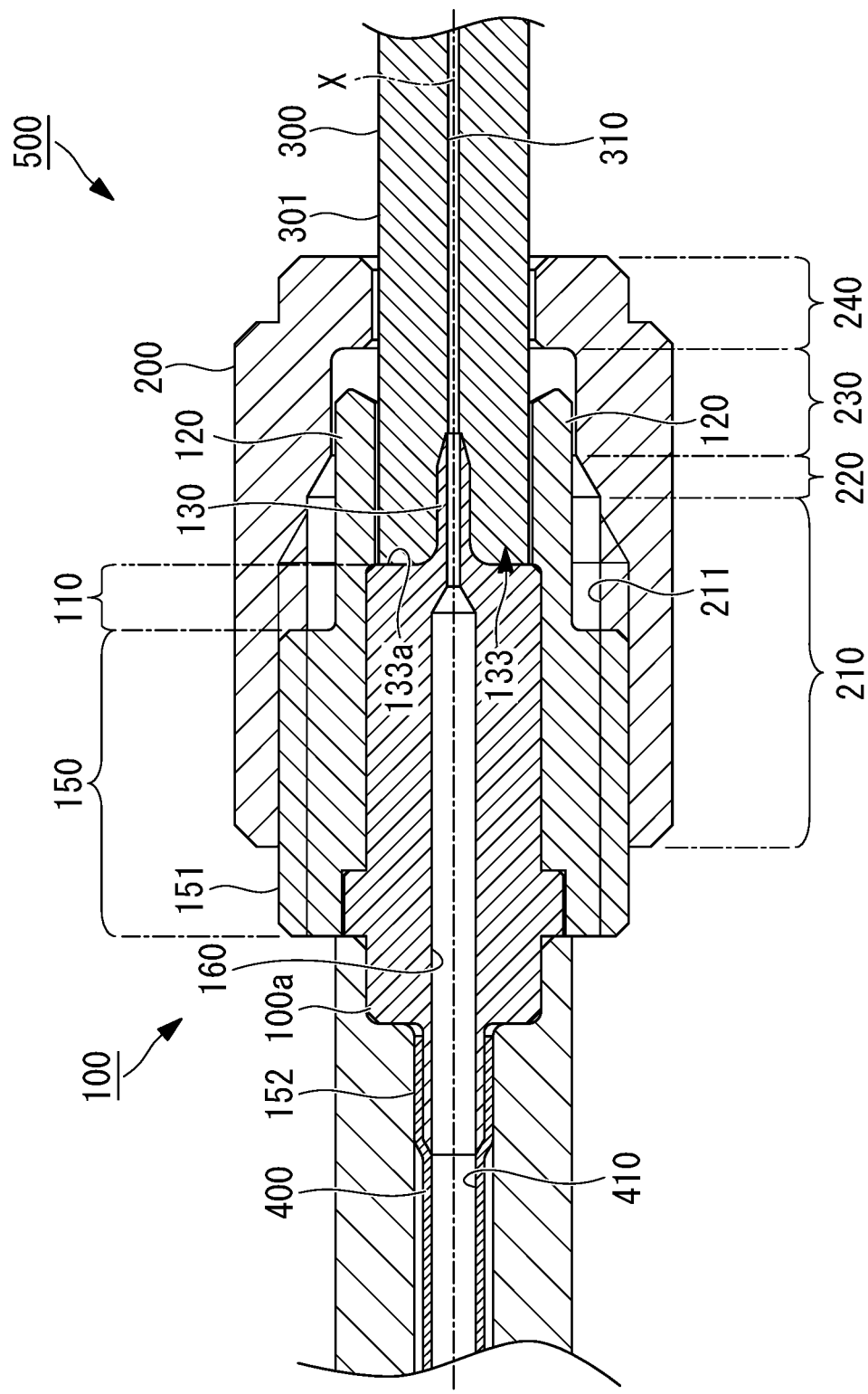
FIG. 7 is a sectional view taken along an arrow B-B of the joint structure illustrated in FIG. 4 and illustrates a state where a nut is being fastened to the joint structure.
Figure 8:
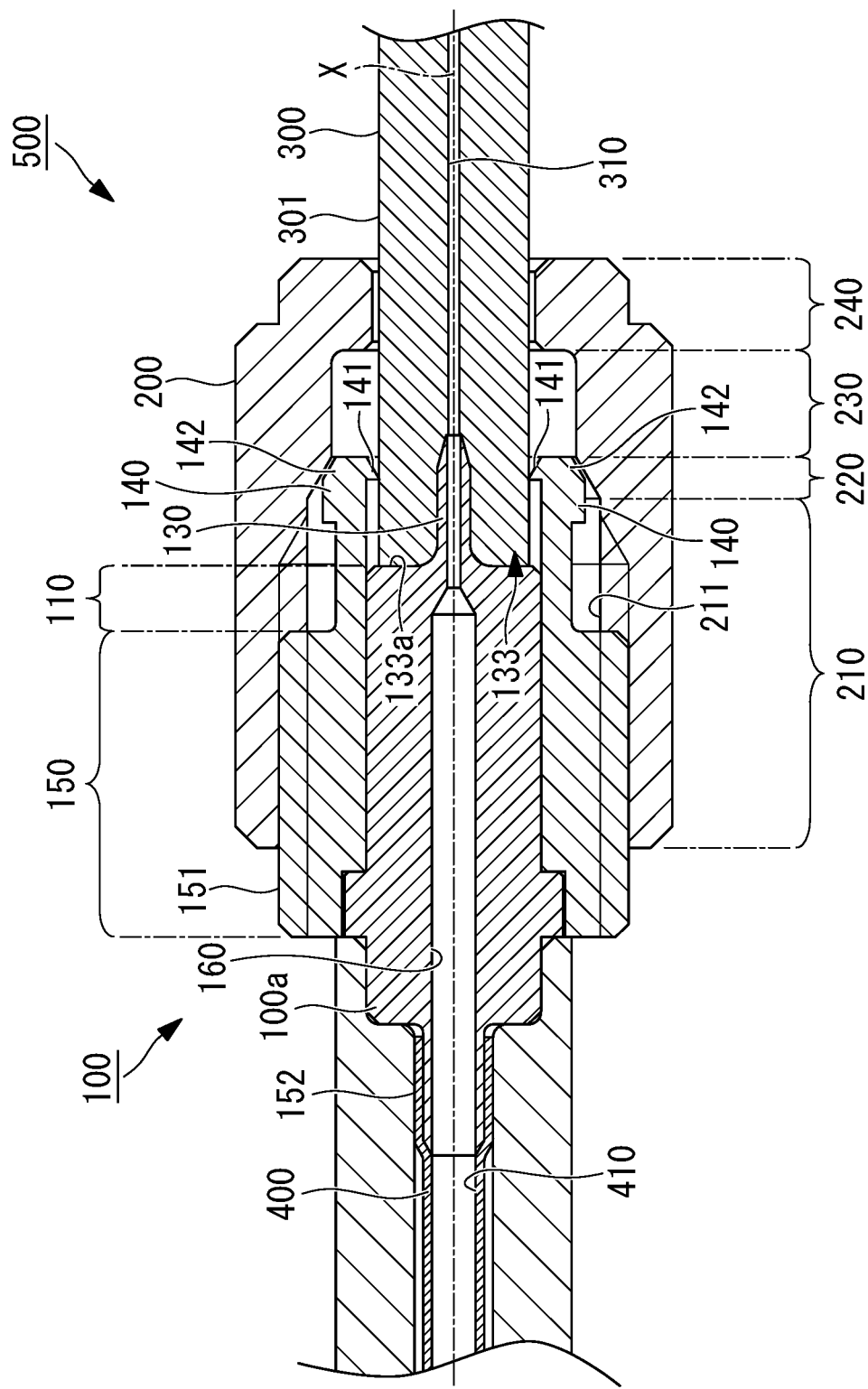
FIG. 8 is a sectional view taken along the arrow C-C of the joint structure illustrated in FIG. 4 and illustrates a state where the nut is being fastened to the joint structure.

Next, the operator attaches the nut 200 to the external thread part 150 of the joint structure 100 by engaging the internal thread 211 with the external thread 151 while rotating the nut 200 about the axis X to have the state illustrated in FIG. 7 and FIG. 8. FIG. 7 is a sectional view taken along the arrow B-B of the joint structure 100 illustrated in FIG. 4 and illustrates a state where the nut 200 is being fastened to the joint structure 100. FIG. 8 is a sectional view taken along the arrow C-C of the joint structure 100 illustrated in FIG. 4 and illustrates a state where the nut 200 is being fastened to the joint structure 100.

As illustrated in FIG. 7, even when the tips of the guide parts 120 enter the inside up to the position of the recessed part 230 of the nut 200, the guide parts 120 do not come into contact with the recessed part 230. The guide parts 120 are secured inside the recessed part 230. On the other hand, as illustrated in FIG. 8, when the tips of the fixing parts 140 enter the inside up to the position of the recessed part 230 of the nut 200, the tips of the fixing parts 140 come into contact with the recessed part 230.

As illustrated in FIG. 8, a contact face 142 is formed to the tip of each fixing part 140, and the distance of the contact face 142 from the axis X in the radial direction gradually decreases toward the tip. The outer diameter of the contact faces 142 on the base end side (the left side in FIG. 8) is larger than the inner diameter ID2 of the recessed part 230. The outer diameter of the contact faces 142 on the tip side (the right side in FIG. 8) is smaller than the inner diameter ID2 of the recessed part 230.

Figure 9:
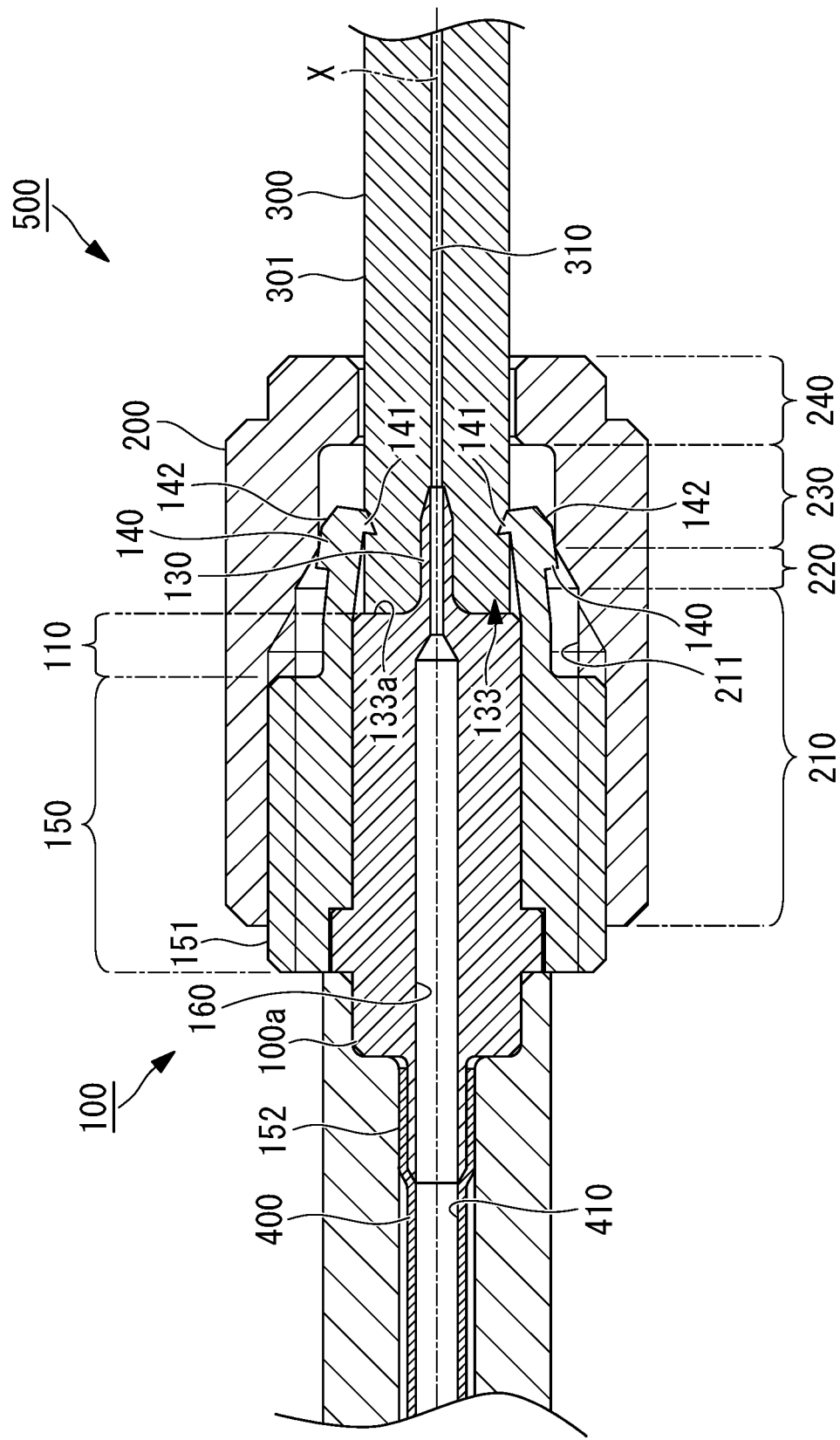
FIG. 9 is a sectional view taken along the arrow B-B of the joint structure illustrated in FIG. 4 and illustrates a state where the nut is fastened to the joint structure.
Figure 10:
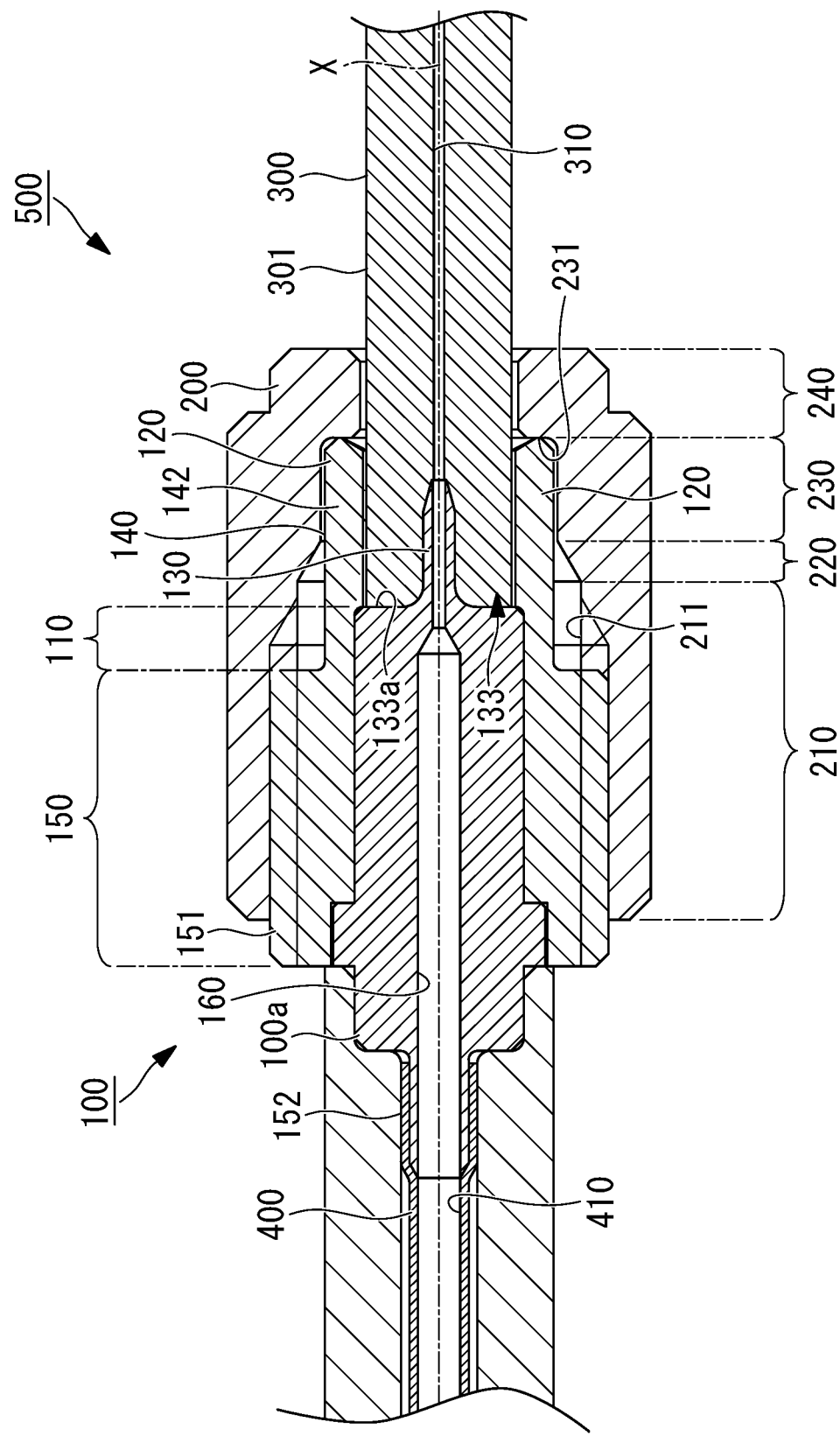
FIG. 10 is a sectional view taken along the arrow C-C of the joint structure illustrated in FIG. 4 and illustrates a state where the nut is fastened to the joint structure.

In a state where a part of the contact faces 142 has entered the recessed part 230, the contact faces 142 come into contact with the end of the recessed part 230 on the coupling part 220 side. When the nut 200 is rotated about the axis X to further engage the internal thread 211 with the external thread 151, the contact faces 142 move toward the axis X due to the contact with the recessed part 230. The biting parts 141 then bite into the outer circumferential face 301 of the resin tube 300 to have the state illustrated in FIG. 9 and FIG. 10 (fixing step). FIG. 9 is a sectional view taken along the arrow B-B of the joint structure 100 illustrated in FIG. 4 and illustrates a state where the nut 200 is fastened to the joint structure 100. FIG. 10 is a sectional view taken along the arrow C-C of the joint structure 100 illustrated in FIG. 4 and illustrates a state where the nut 200 is fastened to the joint structure 100.

As illustrated in FIG. 9, the biting parts 141 provided to the tips of the fixing parts 140 in contact with the recessed part 230 bite into the outer circumferential face 301 of the resin tube 300 in a state where the nut 200 is fastened to the joint structure 100. The biting parts 141 bite into the outer circumferential face 301 and thereby push the tip of the resin tube 300 against the bottom 133a of the insertion groove 133. Since the contact portion between the tip of the resin tube 300 and the bottom 133a makes an annular seal region, this can reliably prevent liquid leakage from the liquid transferring channel 310.

Further, even when the resin tube 300 is pulled in a direction away from the joint structure 100 (a direction toward the right side in FIG. 9) by the biting parts 141, this prevents the resin tube 300 from coming off of the joint structure 100. This is because, even when force to pull out the resin tube 300 works on the biting parts 141, the fixing parts 140 are in contact with the recessed part 230, and therefore, the state where the biting parts 141 have bitten into the outer circumferential face 301 of the resin tube 300 is maintained.

As illustrated in FIG. 10, the recessed part 230 has a bottom 231 against which the tips of the guide parts 120 are abutted. Once the tips of the guide parts 120 are abutted against the button 231, the nut 200 is no longer able to be rotated in a direction in which the nut 200 is fastened to the joint structure 100. Therefore, a resulted state is that the nut 200 is fastened to the joint structure 100 in a state where the tips of the guide parts 120 are abutted to the bottom 231. The operator is no longer able to rotate the nut 200 in a direction in which the nut 200 is fastened to the joint structure 100 and thereby is able to recognize the state where the nut 200 is fastened to the joint structure 100.

Figure 11:
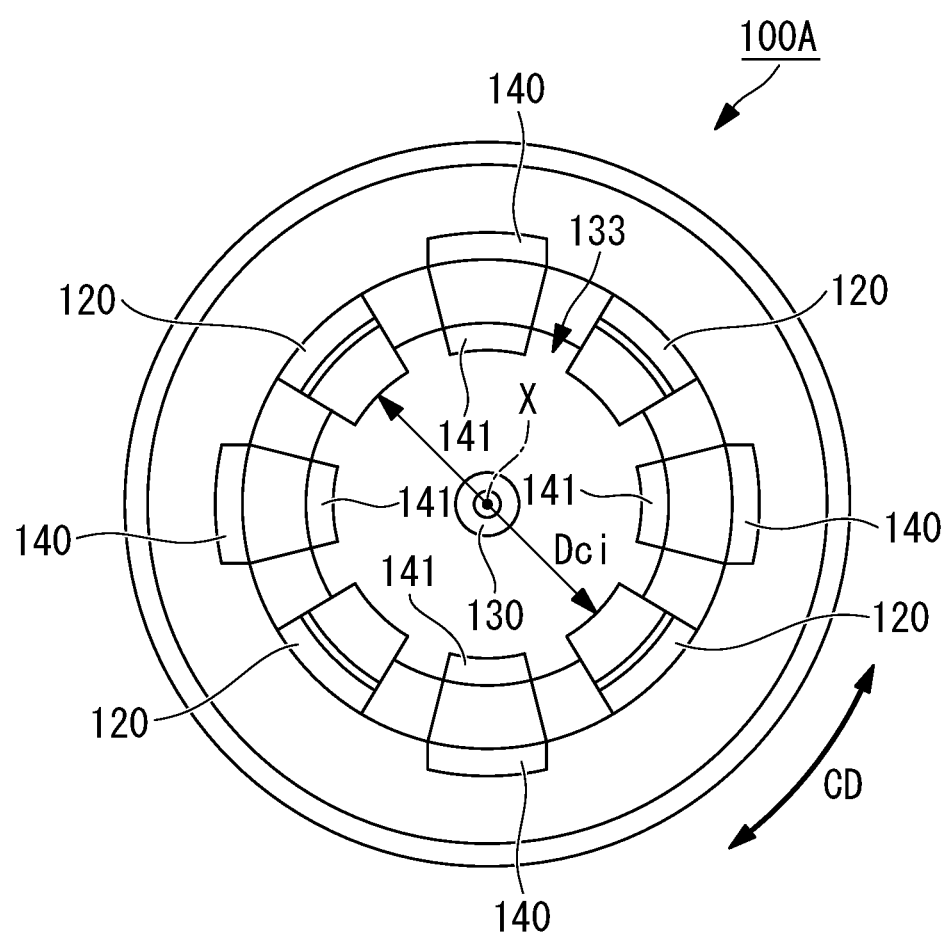
FIG. 11 illustrates a joint structure of a first modified example and is a side view of the joint structure when viewed from the resin tube side.

Although the joint structure 100 in the description above is such that the pair of the guide parts 120 are arranged spaced apart by intervals of 180 degrees in the circumferential direction CD, the pair of the fixing parts 140 are arranged spaced apart by intervals of 180 degrees in the circumferential direction CD, and the guide parts 120 and the fixing parts 140 are arranged alternatingly, another form may be employed. For example, the guide parts 120 and the fixing parts 140 may be arranged as illustrated in FIG. 11. FIG. 11 illustrates a joint structure 100A of a first modified example and is a side view of the joint structure 100A when viewed from the resin tube side.

As illustrated in FIG. 11, in the joint structure 100A of the first modified example, four guide parts 120 are arranged spaced apart by intervals of 90 degrees in the circumferential direction CD, and four fixing parts 140 are arranged spaced apart by intervals of 90 degrees in the circumferential direction CD. The guide parts 120 and the fixing parts 140 are arranged alternatingly. Further, instead of the joint structure 100A of the first modified example, another joint structure may be employed in which three or five or more of multiple guide parts 120 and three or five or more of multiple fixing parts 140 are arranged alternatingly in the circumferential direction CD.

Figure 12:
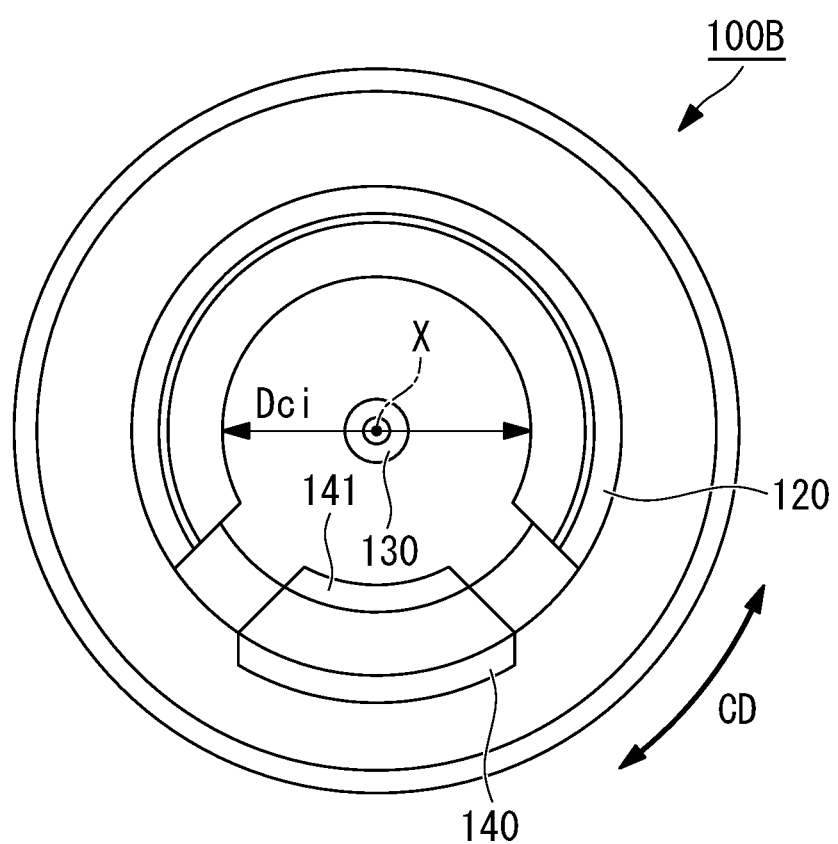
FIG. 12 illustrates a joint structure of a second modified example and is a side view of the joint structure when viewed from the resin tube side.

Further, as illustrated in FIG. 12, a joint structure 100B of a second modified example in which a single guide part 120 and a single fixing part 140 are arranged may be employed. FIG. 12 illustrates the joint structure 100B of the second modified example and is a side view of the joint structure 100B when viewed from the resin tube side. As illustrated in FIG. 12, the joint structure 100B of the second modified example has the guide part 120 arranged in an arc shape in a range larger than 180 degrees in the circumferential direction CD and the fixing part 140 arranged in an arc shape in a range smaller than 180 degrees.

Operations and effects produced by the above described present embodiment will be described.

According to the present embodiment, the joint unit 500 comprises the protrusion 130 that forms the insertion groove 133 in which the resin-made tube 300 is inserted, between the protrusion and the guide part 120 that holds the outer peripheral surface 301 of the resin-made tube 300, and the tip of the protrusion 130 is disposed at the position closer to the main body 110 than the tip of the guide part 120. Consequently, if the end of the resin-made tube 300 is brought close to the joint structure 100, the outer peripheral surface 301 of the resin-made tube 300 is guided by the inner peripheral surface of the tubular part 120 before the end of the resin-made tube 300 comes in contact with the tip 132 of the protrusion 130. The outer peripheral surface 301 of the resin-made tube 300 is guided by the inner peripheral surface of the guide part 120, and the liquid transferring channel 310 formed in the resin-made tube 300 is accordingly disposed on the same axis X as the center axis of the protrusion 130.

In this state, when the operator presses the resin-made tube 300 toward the main body 110 of the joint structure 100, the protrusion 130 disposed on the same axis is inserted in the liquid transferring channel 310. Thus, the operator can easily perform the operation of inserting the protrusion 130 in the liquid transferring channel 310 without visually recognizing the liquid transferring channel 310 formed in the resin-made tube 300.

Further, according to the joint unit 500 of the present embodiment, the nut 200 has the recessed part 230 having the inner diameter ID2 that is larger than the outer diameter OD1 of the guide part 120 and smaller than the outer diameter OD2 of the fixing part 140. Since the inner diameter ID2 of the recessed part 230 is larger than the outer diameter OD1 of the guide part 120, the guide part 120 is secured in the recessed part 230 without the guide part 120 coming into contact with the inner circumferential face of the recessed part 230 when the nut 200 is fastened to the joint structure 100. On the other hand, since the inner diameter ID2 of the recessed part 230 is smaller than the outer diameter OD2 of the fixing part 140, the fixing part 140 comes into contact with the inner circumferential face of the recessed part 230 when the nut 200 is fastened to the joint structure 100.

The tip of the fixing part 140 in contact with the recessed part 230 then bites into the outer circumferential face 301 of the resin tube 300 in a state where the nut 200 is fastened to the joint structure 100. This is because, due to the tip of the fixing part 140 coming into contact with the recessed part 230, the fixing part 140, which is formed in only a part in the circumferential direction CD, is easily deformed toward the inner circumferential side. In such a way, by causing the tip of the fixing part 140 to bite into the outer circumferential face 301 of the resin tube 300, it is possible to reliably exert sufficient holding force for fixing the resin tube 300 so that the resin tube 300 does not come off of the protrusion 130.

According to the joint unit 500 of the present embodiment, with the use of the plurality of guide parts 120 arranged spaced apart by intervals in the circumferential direction CD, it is possible to reliably guide the outer circumferential face 301 of the resin tube 300 and arrange the liquid transferring channel 310 on the same axis X as the center axis of the protrusion 130. Further, the plurality of fixing parts 140, which are arranged between the pair of guide parts 120 arranged adjacent to each other, are arranged spaced apart by intervals in the circumferential direction CD, and this makes it possible to reliably exert sufficient holding force for fixing the resin tube 300 so that the resin tube 300 does not come off of the protrusion 130.

According to the joint unit 500 of the present embodiment, when fastening the nut 200 to the joint structure 100, because the tip of the guide part 120 is abutted to the bottom 231 of the recessed part 230, the operator is able to easily recognize that the nut 200 has been fastened to the joint structure 100, and this makes it possible to prevent the nut 200 from being excessively clamped to the joint structure 100.

According to the joint unit 500 of the present embodiment, the force exerted when the tip of the fixing part 140 is caused to bite into the outer circumferential face 301 of the resin tube 300 is not exerted on a region that is more distant from the main body 110 than the tip 132 of the protrusion 130. It is thus possible to prevent a failure of blockage of the liquid transferring channel 310 resulted from that the resin tube 300 is deformed by the force exerted when the tip of the fixing part 140 is caused to bite into the outer circumferential face 301 of the resin tube 300.

According to the joint unit 500 of the present embodiment, by causing the biting part 141 protruding toward the protrusion 130 in the radial direction to bite into the outer circumferential face 301 of the resin tube 300, it is possible to reliably exert sufficient holding force for fixing the resin tube 300 so that the resin tube 300 does not come off of the protrusion 130.

According to the joint unit 500 of the present embodiment, since the length of the protrusion along the axis is three or more times the outer diameter of the protrusion, the protrusion 130 is a needle-like shape protruding out of the main body 110. By inserting the needle-shape protrusion 130 into the liquid transferring channel 310 of the resin tube 300, it is possible to provide a sufficient length of the seal region between the outer circumferential face of the protrusion 130 and the liquid transferring channel 310. Further, it may be difficult for the operator to insert the needle-shape protrusion 130 in the liquid transferring channel 310 while visually checking the needle-shape protrusion 130, however, since the protrusion 130 is inserted in the liquid transferring channel 310 in a state where the liquid transferring channel 310 and the protrusion 130 are arranged on the same axis, the operator is able to easily perform an operation to insert the protrusion 130 in the liquid transferring channel 310.

According to the joint unit 500 of the present configuration, the length from the tip of the protrusion 130 to the tip of the guide part 120 is 0.2 or more times the inner diameter of the guide part 120. Thus, the end of the resin tube 300 comes into contact with the tip 132 of the protrusion 130 in a state where the end of the resin tube 300 is inserted for a sufficient length to the inner diameter of the guide part 120. It is therefore possible to perform an operation to insert the protrusion 130 in the liquid transferring channel 310 in a state where the outer circumferential face 301 of the resin tube 300 is reliably held by the inner circumferential face of the guide part 120.

According to the joint unit 500 of the present embodiment, since the outer diameter Dto of the resin tube 300 is sufficiently larger than the inner diameter Dti, the resin tube 300 has a sufficient thickness. Thus, even when durability against pressing force is required, sufficient rigidity and associated durability can be exerted. Further, when the resin tube 300 having high rigidity is used, although it is difficult to elastically deform the resin tube 300 by inserting the protrusion 130, it is possible to perform an operation to insert the protrusion 130 in the liquid transferring channel 310 in a state where the outer circumferential face 301 of the resin tube 300 is held by the inner circumferential face of the guide part 120. It is therefore possible to easily insert the protrusion 130 in the resin tube 300.

According to the joint unit 500 of the present embodiment, the inner diameter of the resin tube 300 is an extremely small diameter of 0.1 mm or greater and 1.0 mm or less. Thus, a low flow rate of a liquid passing through the channel formed in the resin tube 300 can be maintained. Further, even when the inner diameter Dti of the resin tube 300 is an extremely small diameter of 0.1 mm or greater and 1.0 mm or less, it is possible to easily perform an operation to insert the protrusion 130 in the liquid transferring channel 310 without visually checking the liquid transferring channel 310 formed in the resin tube 300.

What is claimed is:

1. A joint unit comprising:
   a resin tube in which a liquid transferring channel extending along an axis is formed and whose cross section orthogonal to the axis is circular;
   a joint structure formed in a shaft shape along the axis, having an external thread in an outer circumferential face of the joint structure, and configured to be attached to an end of the resin tube; and
   a nut formed in a cylindrical shape along the axis and having an internal thread formed in an inner circumferential face of the nut, the internal thread being configured to be engaged with the external thread,
   wherein the joint structure comprises
   a main body,
   at least one guide part formed in a part in a circumferential direction about the axis so as to protrude along the axis from the main body and configured to guide an outer circumferential face of the resin tube,
   a protrusion formed in a shaft shape so as to protrude along the axis from the main body and forming an insertion groove between the guide part and the protrusion, the resin tube being inserted in the insertion groove, and
   at least one fixing part formed in a part in the circumferential direction so as to protrude along the axis from the main body and configured to fix the resin tube inserted in the insertion groove,
   wherein a coupling channel extending along the axis and configured to couple the liquid transferring channel and another channel is formed in the main body and the protrusion,
   wherein a tip of the protrusion is located closer to the main body than a tip of the guide part,
   wherein the nut has a recessed part having an inner diameter that is larger than a first outer diameter of the guide part and smaller than a second outer diameter of the fixing part, and
   wherein a tip of the fixing part in contact with the recessed part bites into the outer circumferential face of the resin tube in a state where the nut is fastened to the joint structure.

2. The joint unit according to claim 1,
   wherein the joint structure has a plurality of guide parts arranged spaced apart by intervals in the circumferential direction and a plurality of fixing parts arranged spaced apart by intervals in the circumferential direction, and
   wherein the fixing parts are arranged between a pair of the guide parts arranged adjacent to each other.

3. The joint unit according to claim 1, wherein the recessed part has a bottom against which the tip of the guide part is abutted.

4. The joint unit according to claim 1, wherein the tip of the fixing part is located closer to the main body than the tip of the protrusion.

5. The joint unit according to claim 1, wherein a biting part protruding toward the protrusion in a radial direction orthogonal to the axis and configured to bite into the outer circumferential face of the resin tube is formed at the tip of the fixing part.

6. The joint unit according to claim 1, wherein a length of the protrusion along the axis is three or more times an outer diameter of the protrusion.

7. The joint unit according to claim 1, wherein a length from the tip of the protrusion to the tip of the guide part is 0.2 or more times an inner diameter of the guide part.

8. The joint unit according to claim 1, wherein an outer diameter of the resin tube is 3 or more times and 15 or less times an inner diameter of the resin tube.

9. The joint unit according to claim 8, wherein the resin tube has an inner diameter of 0.1 mm or greater and 1.0 mm or less.

10. A method for assembling a joint unit, wherein the joint unit comprises
- a resin tube in which a liquid transferring channel extending along an axis is formed and whose cross section orthogonal to the axis is circular,
- a joint structure formed in a shaft shape along the axis, having an external thread in an outer circumferential face of the joint structure, and configured to be attached to an end of the resin tube, and
- a nut formed in a cylindrical shape along the axis and having an internal thread formed in an inner circumferential face of the nut, the internal thread being configured to be engaged with the external thread, wherein the joint structure comprises
- a main body,
- a guide part formed so as to protrude along the axis from the main body and configured to guide an outer circumferential face of the resin tube,
- a protrusion formed in a shaft shape so as to protrude along the axis from the main body and forming an insertion groove between the guide part and the protrusion, the resin tube being inserted in the insertion groove, and
- a fixing part formed so as to protrude along the axis from the main body and configured to fix the resin tube inserted in the insertion groove, wherein a coupling channel extending along the axis and configured to couple the liquid transferring channel and another channel is formed in the main body and the protrusion, wherein a tip of the protrusion is located closer to the main body than a tip of the guide part, and wherein the nut has a recessed part having an inner diameter that is larger than a first outer diameter of the guide part and smaller than a second outer diameter of the fixing part, the method comprising:

an insertion step of guiding the outer circumferential face of the resin tube by the guide part and inserting the protrusion in the liquid transferring channel; and a fixing step of fastening the nut to the joint structure to cause the fixing part to come into contact with the recessed part and cause the tip of the fixing part to bite into the outer circumferential face of the resin tube.

* * * * *